(12) United States Patent
Kimura et al.

(10) Patent No.: US 12,109,026 B2
(45) Date of Patent: Oct. 8, 2024

(54) EXERCISE LOAD CONTROL DEVICE

(71) Applicant: Mitsubishi Electric Engineering Company, Limited, Tokyo (JP)

(72) Inventors: Yuichi Kimura, Tokyo (JP); Isao Mizukura, Tokyo (JP)

(73) Assignee: MITSUBISHI ELECTRIC ENGINEERING COMPANY, LIMITED, Tokyo (JP)

( * ) Notice: Subject to any disclaimer, the term of this patent is extended or adjusted under 35 U.S.C. 154(b) by 383 days.

(21) Appl. No.: 17/605,577

(22) PCT Filed: May 27, 2019

(86) PCT No.: PCT/JP2019/020868
§ 371 (c)(1),
(2) Date: Oct. 22, 2021

(87) PCT Pub. No.: WO2020/240651
PCT Pub. Date: Dec. 3, 2020

(65) Prior Publication Data
US 2022/0202331 A1 Jun. 30, 2022

(51) Int. Cl.
*A61B 5/22* (2006.01)
*A63B 22/06* (2006.01)

(52) U.S. Cl.
CPC .......... *A61B 5/222* (2013.01); *A63B 22/0605* (2013.01); *A61B 2505/09* (2013.01); *A63B 2220/17* (2013.01)

(58) Field of Classification Search
CPC . A61B 5/222; A61B 2505/09; A63B 22/0605; A63B 2220/17;
(Continued)

(56) References Cited

U.S. PATENT DOCUMENTS

| | | | |
|---|---|---|---|
| 8,951,168 B2* | 2/2015 | Baudhuin | G16H 40/20 482/8 |
| 2010/0022354 A1* | 1/2010 | Fisher | A63B 71/0622 482/8 |
| 2012/0004074 A1* | 1/2012 | Schelzig | A63B 24/0087 482/4 |

(Continued)

FOREIGN PATENT DOCUMENTS

EP  0485981 A2  5/1992
EP  2870915 A1  5/2015
(Continued)

OTHER PUBLICATIONS

Japanese Notice of Reasons for Refusal issued Jul. 5, 2022, in Japanese Application No. 2021-521583.
(Continued)

*Primary Examiner* — Nyca T Nguyen
(74) *Attorney, Agent, or Firm* — XSENSUS LLP

(57) ABSTRACT

Provided is an exercise load control device including: a patient information input unit configured to input patient information which indicates whether a patient using an exercise therapy apparatus is an atrial fibrillation patient; a heart rate information acquisition unit configured to acquire heart rate information which indicates a heart rate of the patient using the exercise therapy apparatus; and a load control unit configured to control a magnitude of a load to be applied by the exercise therapy apparatus to the patient, based on the patient information input by the patient information input unit and the heart rate information acquired by the heart rate information acquisition unit.

4 Claims, 15 Drawing Sheets

(58) Field of Classification Search
CPC ...... A63B 2024/0093; A63B 21/00181; A63B 21/0059; A63B 24/0087; A63B 2230/062
See application file for complete search history.

(56) References Cited

U.S. PATENT DOCUMENTS

| | | | |
|---|---|---|---|
| 2015/0128695 A1* | 5/2015 | Tai | A61B 5/6826 73/379.01 |
| 2016/0166881 A1* | 6/2016 | Ridgel | A61B 5/6895 482/7 |
| 2017/0095670 A1 | 4/2017 | Ghaffari et al. | |
| 2017/0216706 A1 | 8/2017 | Bleich et al. | |
| 2017/0274250 A1* | 9/2017 | Itoh | A61B 5/742 |
| 2021/0038088 A1* | 2/2021 | Atallah | A61B 3/112 |

FOREIGN PATENT DOCUMENTS

| | | |
|---|---|---|
| JP | H10-137362 A | 5/1998 |
| JP | 2002-345996 A | 12/2002 |
| JP | 2018-166935 A | 11/2018 |
| WO | 01/52738 A1 | 7/2001 |

OTHER PUBLICATIONS

International Search Report and Written Opinion mailed on Aug. 20, 2019, received for PCT Application PCT/JP2019/020868, Filed on May 27, 2019, 9 pages including English Translation.

Extended European search report issued on Dec. 5, 2022, in corresponding European patent Application No. 19930675.4, 7 pages.

* cited by examiner

EXERCISE LOAD CONTROL DEVICE

CROSS-REFERENCE TO RELATED APPLICATION

The present application is based on PCT filing PCT/JP2019/020868, filed May 27, 2019, the entire contents of which are incorporated herein by reference.

TECHNICAL FIELD

The present invention relates to an exercise load control device to be used in an exercise therapy apparatus.

BACKGROUND ART

Exercise therapy plays a central role in cardiac rehabilitation of heart disease patients. Ergometers, treadmills, and other exercise therapy apparatus are used for that kind of cardiac rehabilitation. Some of the exercise therapy apparatus are configured to assist an exerciser in a constant heart rate exercise by measuring an exercise physiological response with a sensor attached to the exerciser's ear, wrist, chest, or other body parts, and controlling load intensity so that a measured value of the response approaches a fixed target value set in advance (for example, Patent Literature 1). The length of time required for the exerciser's heart rate to shift with a change in exercise load varies depending on a response time constant of the exerciser's exercise physiological response. An exercise therapy apparatus in which a response time constant can be set has accordingly been commercialized (see, for example, Patent Literature 2).

CITATION LIST

Patent Literature

[PTL 1] JP 63-35254 A
[PTL 2] JP 2015-177873 A

SUMMARY OF INVENTION

Technical Problem

Constant heart rate control is considered to be desirable for heart disease patients in terms of safety and burden on the heart from the load. In the constant heart rate control, the load intensity is determined from a deviation that is a difference between the exerciser's heart rate and a target heart rate. The determination of the load intensity is executed by an exercise load control device used in exercise therapy apparatus. Proportional-integral (PI) control based on a deviation between a target value of the heart rate and a current value of the heart rate, or similar feedback control, is normally used in the determination of the load intensity.

There are various types of heart diseases. Arrhythmia patients, in particular, patients with atrial fibrillation (AF) tend to have large fluctuations in measured heart rate, that is, great ups and downs of heart rate, compared to patients with the other heart diseases. AF patients are also slow in heart rate response to a change in exercise load. For example, when the load intensity is changed in steps, heart rates of AF patients often take about two to three times longer than heart rates of patients with the other heart diseases to rise. In addition to a rise period, heart rates of AF patients in a steady heart rate period respond differently from those of patients with the other heart diseases to a difference in exercise load.

It is therefore considered that AF patients in particular are preferred to be differentiated from patients with the other heart diseases. This is because large fluctuations in heart rate and a heart rate response speed are factors for the determination of the load intensity by PI control. A deviation between the exerciser's heart rate and a target heart rate that is used in PI control is changed by large fluctuation in heart rate and the heart rate response speed. An inappropriately determined load intensity not only hinders the exerciser from exercising comfortably but may also place an excessive burden.

It is assumed that an exercise therapy apparatus is used by patients with various heart diseases. The exercise therapy apparatus is adaptable on a heart disease patient-by-heart disease patient basis by changing constants used as coefficients in PI control. A change of the constants, however, decreases stability in feedback control when improvement in response is aimed at increasing an exercise time at a constant heart rate within a prescribed exercise time of the patient and, at worst, has the risk of causing the patient's heart rate to oscillate, thus requiring to be performed by an exerciser's supervisor who has not only medical knowledge but also knowledge of control engineering. Varying of the constants on a heart disease patient-by-heart disease patient basis therefore has an aspect of, in addition to hindering comfortable use of the exercise therapy apparatus, increasing the supervisor's, or a similar person's, burden of searching for constants of an integral term and a proportional term in feedback control that are appropriate coefficients suited to the patient.

The present invention has been made to solve the above-mentioned problems, and an object thereof is therefore to provide an exercise load control device that improves user friendliness of an exercise therapy apparatus even more for a patient with a heart disease.

Solution to Problem

According to one embodiment of the present invention, there is provided an exercise load control device including: a patient information input unit configured to input patient information which indicates whether a patient using an exercise therapy apparatus is an atrial fibrillation patient; a heart rate information acquisition unit configured to acquire heart rate information which indicates a heart rate of the patient using the exercise therapy apparatus; and a load control unit configured to control a magnitude of a load to be applied by the exercise therapy apparatus to the patient, based on the patient information input by the patient information input unit and the heart rate information acquired by the heart rate information acquisition unit.

Advantageous Effects of Invention

According to the present invention, it is possible to improve user friendliness of the exercise therapy apparatus even more for the patient with a heart disease.

DESCRIPTION OF EMBODIMENTS

An exercise load control device according to an embodiment of the present invention is described below with reference to the drawings.

First Embodiment

Figure 1:
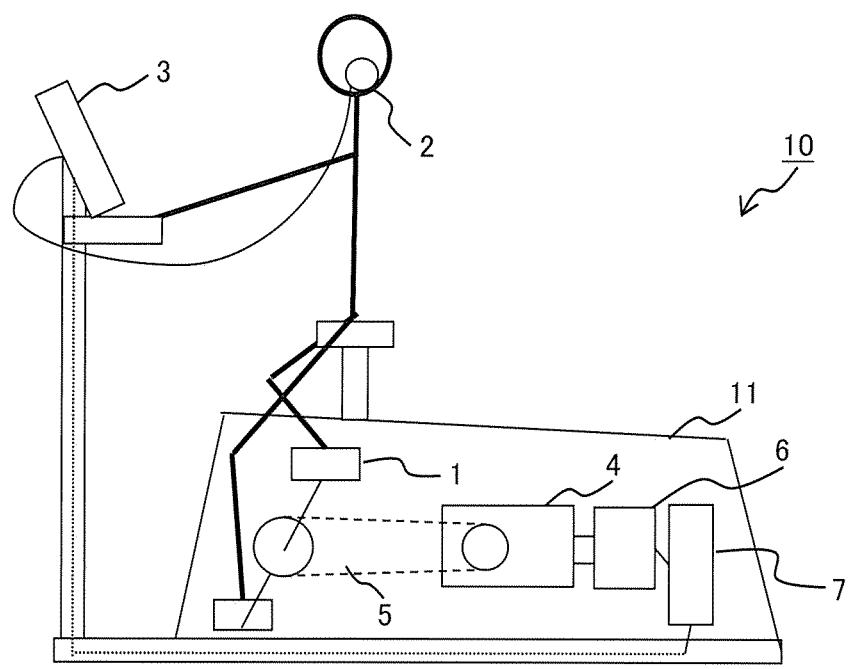
FIG. 1 is a diagram for illustrating an example of a configuration of an exercise therapy apparatus to which an exercise load control device according to a first embodiment of the present invention is applied.

FIG. 1 is a diagram for illustrating an example of a configuration of an exercise therapy apparatus to which an exercise load control device according to a first embodiment of the present invention is applied. An exercise therapy apparatus 10 is a cycling ergometer for an exercise involving pedaling pedals 1 by an exerciser. As illustrated in FIG. 1, the exercise therapy apparatus 10 includes, in addition to the pedals 1, a heart rate detection sensor 2, an operating unit 3, a decelerator 4, a transmission mechanism 5, a motor 6, and a load driving device 7. The pedals 1, the operating unit 3, the decelerator 4, the transmission mechanism 5, the motor 6, and the load driving device 7 form a main body of the exercise therapy apparatus 10. The exercise therapy apparatus is not limited to ergometers.

The heart rate detection sensor 2 is configured to output, to the operating unit 3, heat rate information indicating a measured heart rate of an exerciser to whom the heat rate detection sensor 2 is attached, each time a set cycle, for example, arrives. The operating unit 3 is configured to display various types of information to the exerciser or other persons, and enable the exerciser or other persons to execute, among others, inputting of various types of information.

The motor 6 is a source of power for applying an exercise load on the exerciser. The load driving device 7 is configured to receive, from the operating unit 3, a load command value which is a command value specifying a load, and drive the motor 6 following the input load command value. The decelerator 4 to which a rotational force of the motor 6 is transmitted is configured to adjust a rotational speed of the motor 6. The rotational force transmitted from the motor 6 to the transmission mechanism 5 is transmitted to the pedals 1 via the transmission mechanism 5.

Figure 2:
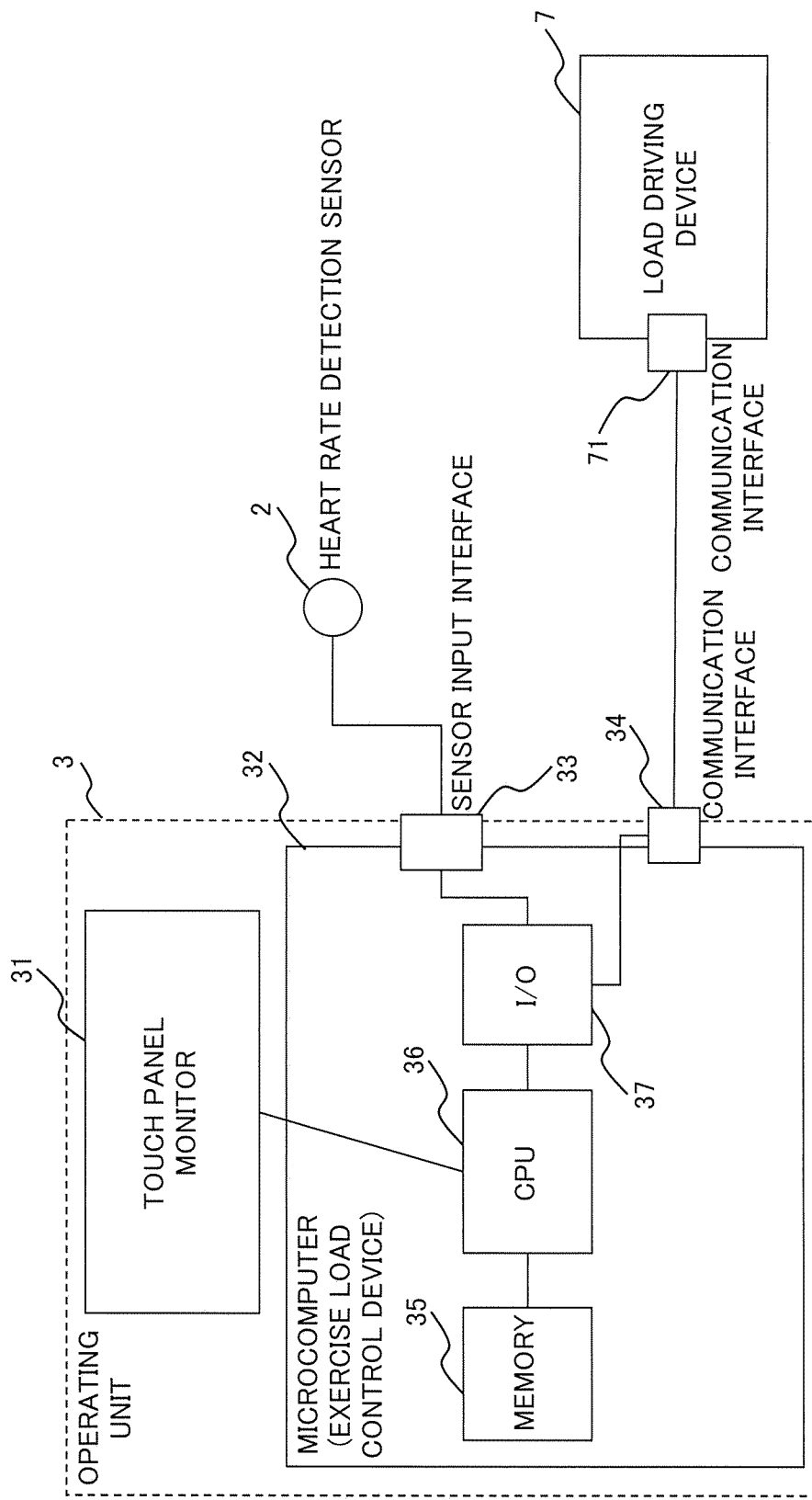
FIG. 2 is a diagram for illustrating an example of a hardware configuration of an operating unit.

FIG. 2 is a diagram for illustrating an example of a hardware configuration of the operating unit. As illustrated in FIG. 2, the operating unit 3 includes a touch panel monitor 31 and a microcomputer 32. The microcomputer 32 is connected to a sensor input interface 33 for input of a signal from the heart rate detection sensor 2 and a communication interface 34 for communication to and from the load driving device 7. The load driving device 7 is provided with a communication interface 71 as well. The communication interface 34 and the communication interface 71 are connected to each other by a cable.

The touch panel monitor 31 is a combination of a monitor that is a display device and a touch panel arranged on a screen of the monitor. The touch panel monitor 31 can thus be used for display of various types of information and input of various types of information.

The microcomputer 32 is an information processing device configured to control the touch panel monitor 31 to display various types of information and deal with operation performed on the touch panel monitor 31. The microcomputer 32 is configured to control the exercise load of the exerciser by determining the load command value to be output to the load driving device 7, and outputting the determined load command value to the load driving device 7. The microcomputer 32 corresponds to the exercise load control device in this embodiment.

As illustrated in FIG. 2, the microcomputer 32 includes a memory 35, a central processing unit (CPU) 36, and an interface controller 37. The memory 35 is a component including, for example, a plurality of types of memories that are a non-volatile memory, a volatile memory, and the like. The non-volatile memory is used to store a program to be executed by the CPU 36 and various types of data. The CPU 36 is configured to perform overall control of the exercise therapy apparatus 10 by reading out and executing the program that is stored in the memory 35. The interface controller 37 implements communication between the CPU 36 and the heart rate detection sensor 2 and communication between the CPU 36 and the load driving device 7.

Figure 3:
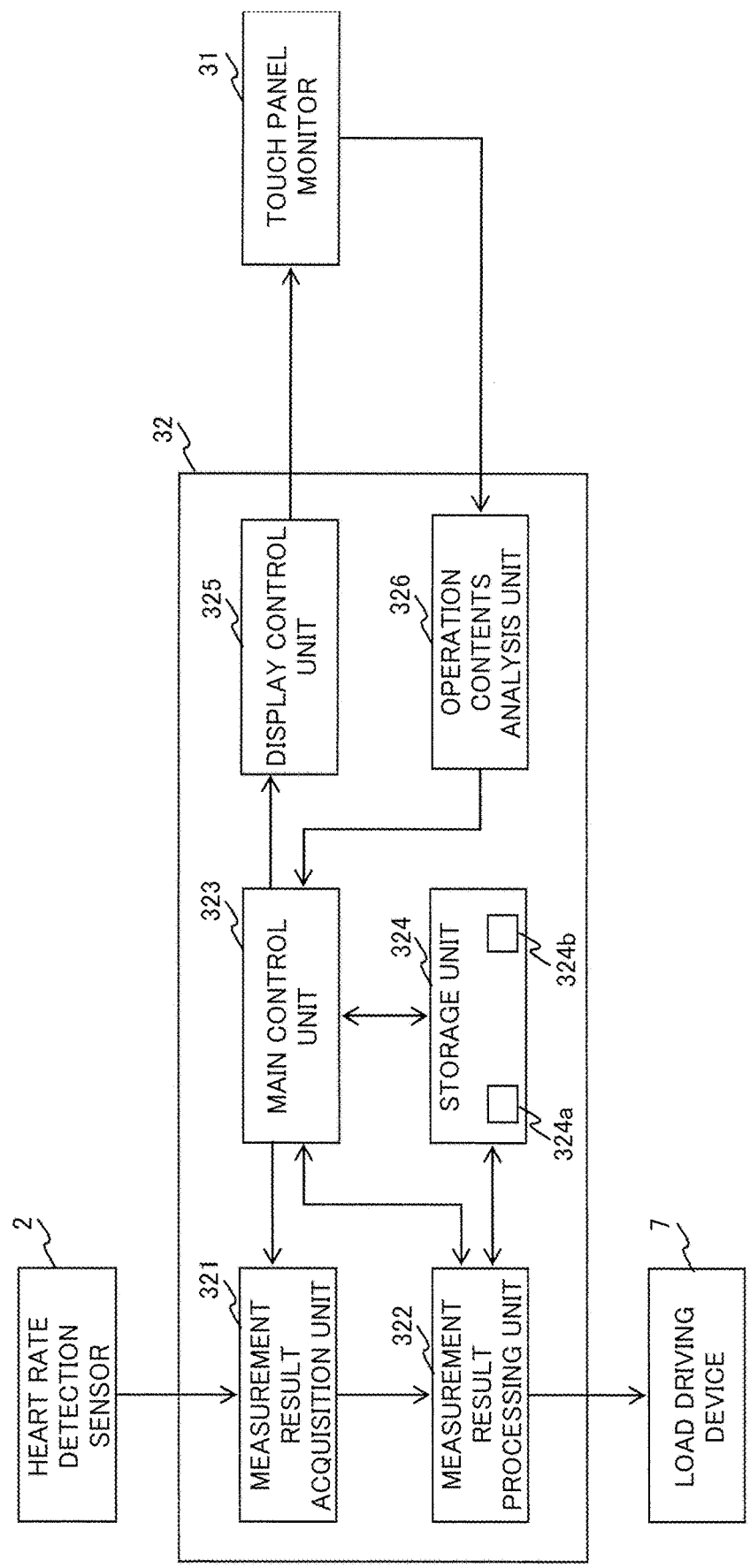
FIG. 3 is a diagram for illustrating an example of a function configuration of the exercise load control device according to the first embodiment of the present invention.

FIG. 3 is a diagram for illustrating an example of a function configuration of the microcomputer, that is, the exercise load control device according to the first embodiment of the present invention. As illustrated in FIG. 3, the microcomputer 32 includes, as function components, a measurement result acquisition unit 321, a measurement result processing unit 322, a main control unit 323, a storage unit 324, a display control unit 325, and an operation contents analysis unit 326.

The measurement result acquisition unit 321 is configured to acquire, as a measurement result, heart rate information output as a signal from the heart rate detection sensor 2. The measurement result processing unit 322 is configured to process the heart rate information acquired by the measurement result acquisition unit 321, to generate various types of data including the load command value.

The load command value generated by the measurement result processing unit 322 is output to the load driving device 7. The measurement result acquisition unit 321 corresponds to the heart rate information acquisition unit in this embodiment. The measurement result processing unit 322 corresponds to the load control unit in this embodiment in a narrow sense. The measurement result acquisition unit 321 may be configured to calculate the exerciser's heart rate with the use of information output as a signal from the heart rate detection sensor 2.

The main control unit 323 is configured to perform overall control of the microcomputer 32. The storage unit 324 is used to store various types of information and various types of data. The various types of data include two parameter groups, namely, parameter groups 324a and 324b. In this embodiment, heart disease patients are divided into AF patients and non-AF patients. The parameter group 324a is for AF patients, and the parameter group 324b is for heart disease patients other than AF patients. Details thereof are described later.

The main control unit 323 determines whether the exerciser is an AF patient, and notifies the result of the determination to the measurement result processing unit 322. This prompts the measurement result processing unit 322 to read at least one of the parameter groups 324a or 324b out of the storage unit 324, and the read parameters are used to process the heart rate information and generate various types of data. The measurement result processing unit 322 therefore varies contents of control for applying a load to a heart disease patient who uses the exercise therapy apparatus 10 as an exerciser, depending on whether the heart disease patient is an AF patient.

The display control unit 325 follows an instruction from the main control unit 323 to display data input from the main control unit 323 on the touch panel monitor 31. The touch panel monitor 31 is configured to output operation information indicating a point at which the touch panel monitor 31 has been operated by a user, and a type of the operation. The operation contents analysis unit 326 is configured to analyze the operation information input from the touch panel monitor 31 to identify contents of the operation performed by the user. The identified contents of the operation are notified to the main control unit 323. The main control unit 323 thus uses the contents of the operation notified from the operation contents analysis unit 326 to execute an update of contents displayed on the touch panel monitor 31, a change of contents of control of the exercise therapy apparatus 10, and the like as required. The user here is mainly a heart disease patient assumed as an exerciser, or a supervisor who supervises the heart disease patient. The term "user" is used to indicate that a person other than the exerciser is included in the meaning.

When the microcomputer 32 has a hardware configuration as the one illustrated in FIG. 2, the measurement result acquisition unit 321 is implemented by the memory 35, the CPU 36, the interface controller 37, and the sensor input interface 33. Similarly, the measurement result processing unit 322 is implemented by the memory 35, the CPU 36, the interface controller 37, and the communication interface 34. The main control unit 323, the display control unit 325, and the operation contents analysis unit 326 are all implemented by the memory 35 and the CPU 36. The storage unit 324 is the memory 35.

Figure 4:
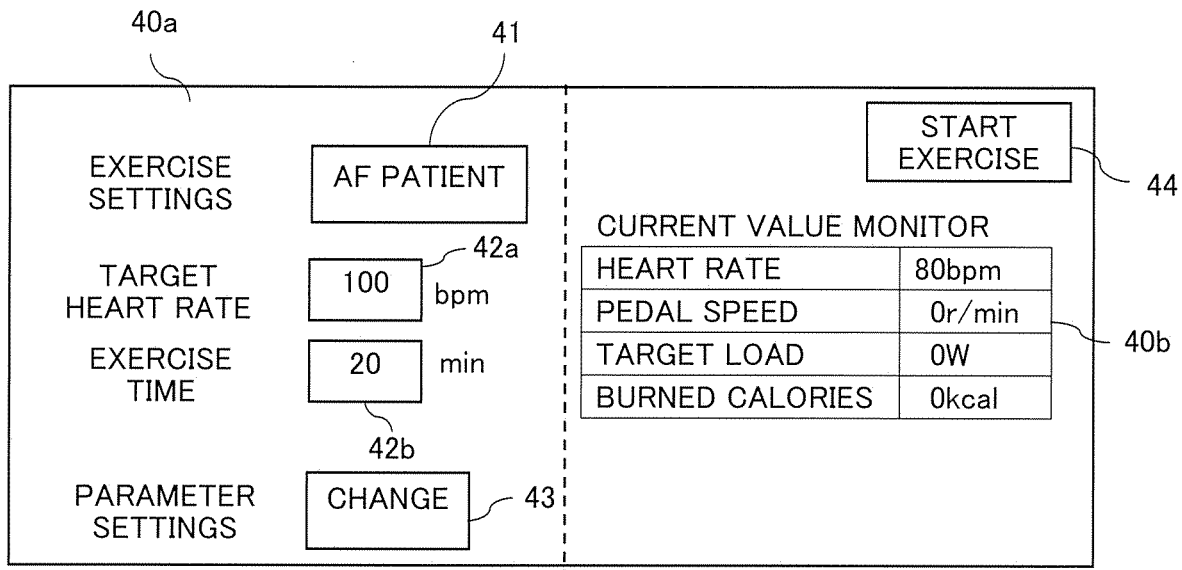
FIG. 4 is a diagram for illustrating an example of a normal screen.
Figure 5:
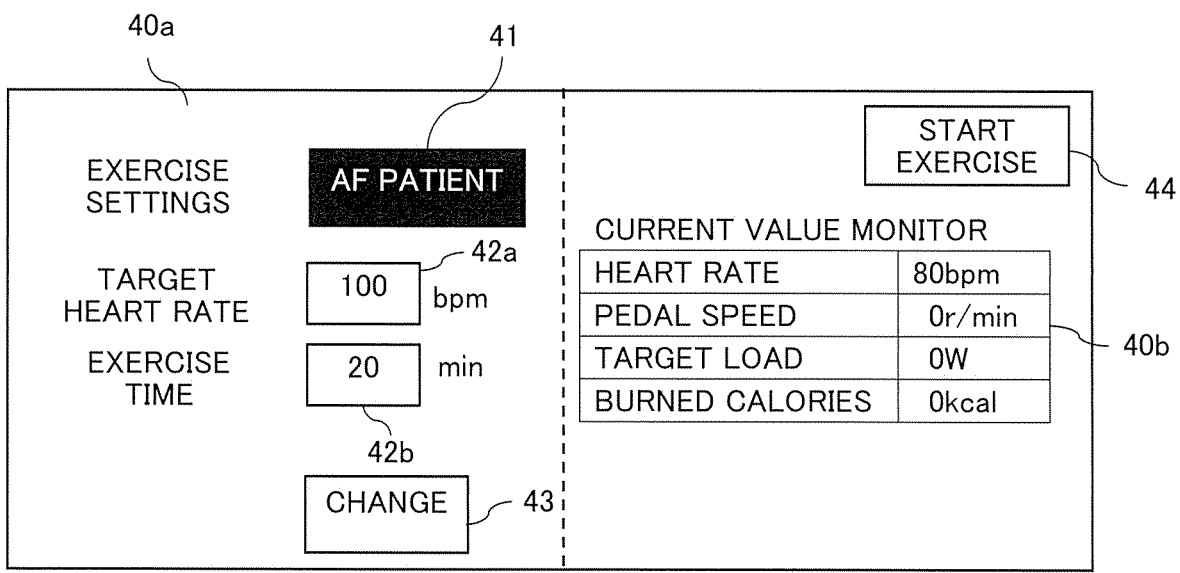
FIG. 5 is a diagram for illustrating an example of the normal screen after an AF patient button is operated.
Figure 6:
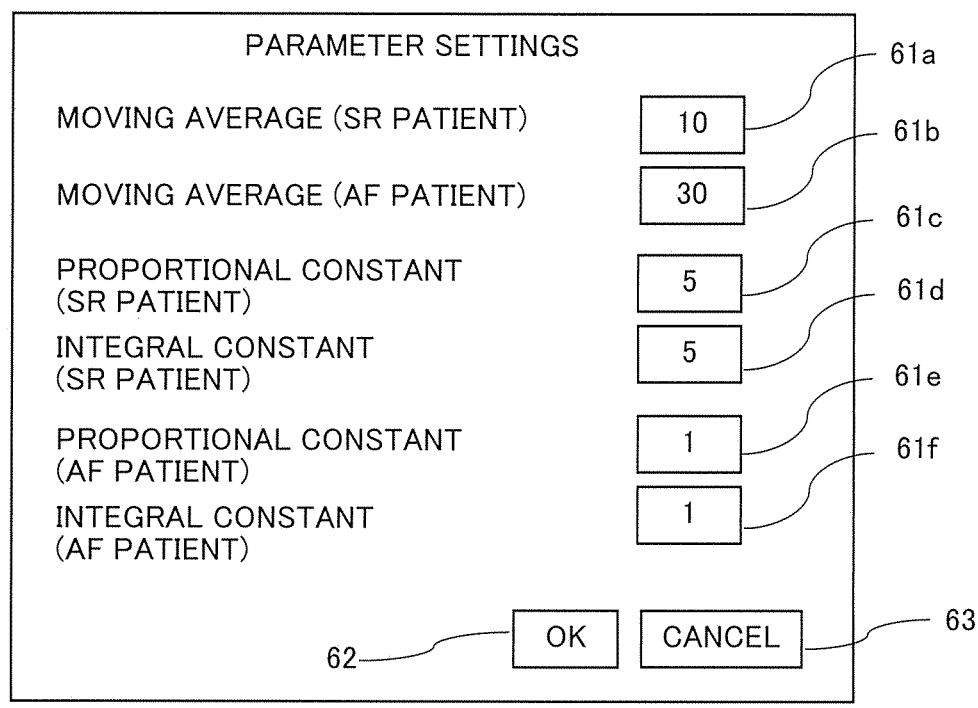
FIG. 6 is a diagram for illustrating an example of a parameter setting screen.

FIG. 4 to FIG. 6 are each a diagram for illustrating an example of a user interface to be displayed on the touch panel monitor. A specific description is given next with reference to FIG. 4 to FIG. 6 on an example of screens to be displayed as a user interface on the touch panel monitor 31.

FIG. 4 is a diagram for illustrating an example of a normal screen. The normal screen is a screen displayed first after the exercise therapy apparatus 10 is activated. The normal screen is, as illustrated in FIG. 4, divided into two areas, namely, areas 40a and 40b.

The area 40a is an area for various settings at which exercise therapy is to be performed. As illustrated in FIG. 4, an AF patient button 41, two input boxes, namely, input boxes 42a and 42b, and a change button 43 are arranged in the area 40a.

AF patients who form a part of arrhythmia patients are characterized in that fluctuations in heart rate are large and rapid, and in that the heart rate takes long to change with switching of an exercise load, compared to patients with other heart diseases. For that reason, heart disease patients are divided into AF patients and non-AF patients in this embodiment. The AF patient button 41 is a button for inputting whether the exerciser is an AF patient. Patient information in this embodiment thus corresponds to data that is input by operating, or not operating, the AF patient button 41. This data input requires display of the AF patient button 41 and determination of whether the AF patient button 41 has been operated. Accordingly, a patient information input unit in this embodiment corresponds to the main control unit 323, the display control unit 325, and the operation contents analysis unit 326 in the function configuration illustrated in FIG. 3. Heart disease patients other than AF patients are hereinafter referred to as "sinus rhythm (SR) patients."

The input box 42a is a box for inputting target heart rate data. The input box 42b is a box for inputting exercise time data. The change button 43 is a button for changing parameter settings. A parameter setting screen which is a different screen can be displayed by operating the change button 43. The target heart rate which can be input as data via the input box 42a corresponds to the target value in this embodiment.

The area 40b is an area for displaying data to be provided to the exerciser during exercise therapy. As illustrated in FIG. 4, a "start exercise" button 44 for instructing the start of exercise therapy is placed in the area 40b. Pieces of data that are a heart rate, a pedal speed, a target load, and burned calories are displayed in the area 40b.

Load control conforms to the contents displayed in the area 40a. In the example illustrated in FIG. 4, the exercise load is controlled so that the exerciser's heart rate maintains 100 beats per minute (bpm) set as the target heart rate for 20 minutes set as the exercise time.

FIG. 5 is a diagram for illustrating an example of the normal screen after the AF patient button is operated. It is shown in FIG. 5 that a change to highlighted display of the AF patient button 41 has been caused by operating, more specifically, clicking, the AF patient button 41. Highlighted display of the AF patient button 41 indicates that data identifying the exerciser as an AF patient has been input. When the highlighted AF patient button 41 is operated again, the AF patient button 41 is changed back to normal display illustrated in FIG. 4. This enables the user of the exercise therapy apparatus 10 to check, based on a display state of the AF patient button 41, input of data identifying the exerciser as an AF patient, that is, contents of settings regarding whether the exerciser is an AF patient.

The data indicating whether the exerciser is an AF patient may be input by the user by a method other than the operation of the AF patient button 41. For example, an SR patient button may be placed in addition to the AF patient button 41 so that the user inputs the data indicating whether the exerciser is an AF patient by operating one of the buttons. When each patient is supposed to carry a card recording personal information about the patient, the touch panel monitor 31 may be substituted with a card reader capable of reading the personal information recorded on the card. Various modifications are thus possible with regards to input of the data indicating whether the exerciser is an AF patient.

FIG. 6 is a diagram for illustrating an example of the parameter setting screen. The parameter setting screen is, as described above, a screen displayed by operating the change button 43 on the normal screen. As illustrated in FIG. 6, input boxes 61a to 61f for inputting parameters are arranged on the parameter setting screen. An OK button 62 and a cancel button 63 are arranged on the parameter setting screen as well.

In this embodiment, the load intensity, that is, the load command value, is determined by proportional-integral (PI) control. For that reason, as illustrated in FIG. 6, the parameter setting screen is designed so that a proportional constant and an integral constant can be set for AF patients and for SR patients separately. The proportional constant is a coefficient by which a deviation that is a difference between the exerciser's measured heart rate and a target heart rate is multiplied. The integral constant is a coefficient by which an integral value obtained with the use of the deviation is multiplied. In this embodiment, the proportional constant corresponds to a first coefficient and the integral constant corresponds to a second coefficient.

As described above, the storage unit 324 illustrated in FIG. 3 stores the two parameter groups, namely, the parameter groups 324a and 324b. The parameter group 324a is, for example, data including a plurality of parameters designed for SR patients, that is, a moving average, a proportional constant, and an integral constant. The other parameter group 324b is a parameter group including a moving average, a proportional constant, and an integral constant that are designed for AF patients.

In this embodiment, an increment/decrement of the load command value is determined by PI control. The integral constant is a coefficient by which the increment and the decrement are each multiplied. Then, when the proportional constant is given as Kp, the integral constant is given as Ki, and the deviation is given as HRd, an increment/decrement ΔW is calculated by, for example, the following expression.

$$\Delta W = Kp \cdot HRd + \Sigma(Ki \cdot HRd) \quad (1)$$

When the load command value is given as W, the load command value W is calculated by Expression (2).

$$W = W + \Delta W \quad (2)$$

This embodiment is further configured so that the moving average can be set for AF patients and for SR patients separately. The OK button 62 is a button for instructing storage of numerical values displayed in the input boxes 61a to 61f as new parameters. The cancel button 63 is a button for instructing invalidation of numerical values displayed in the input boxes 61a to 61f. When the cancel button 63 is operated, numerical values displayed in the input boxes 61a to 61f are cleared without being used for an update of the parameters.

Figure 7:
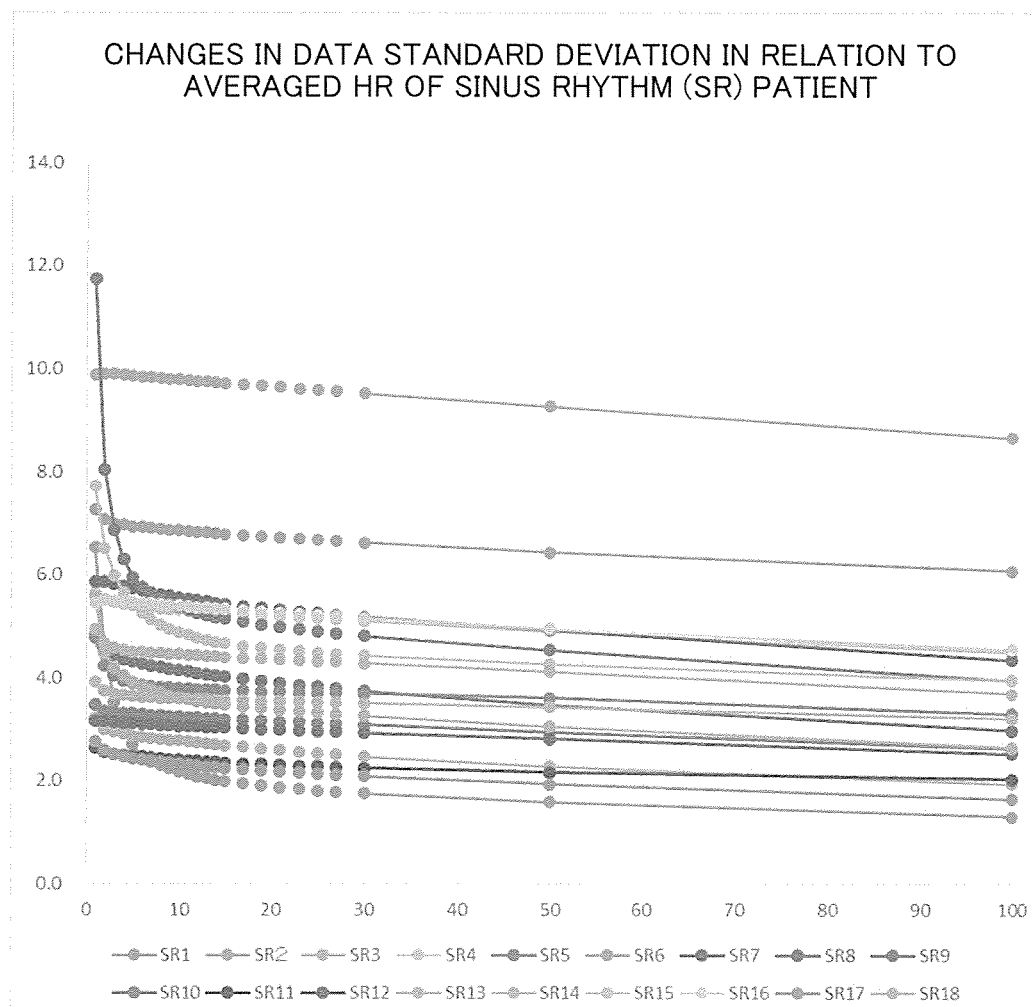
FIG. 7 is a graph for showing an example of changes in standard deviation in relation to a moving average of a heart rate of an SR patient.
Figure 8:
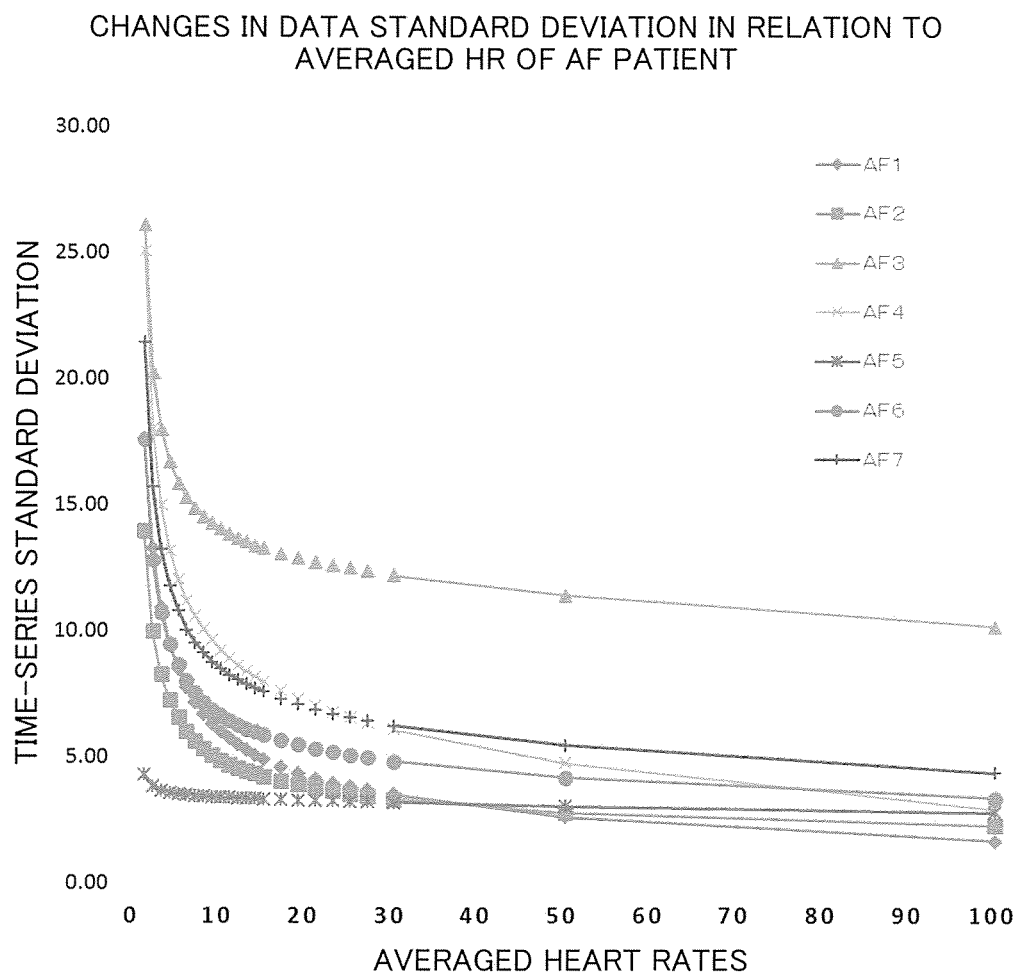
FIG. 8 is a graph for showing an example of changes in standard deviation in relation to a moving average of a heart rate of an AF patient.
Figure 9:
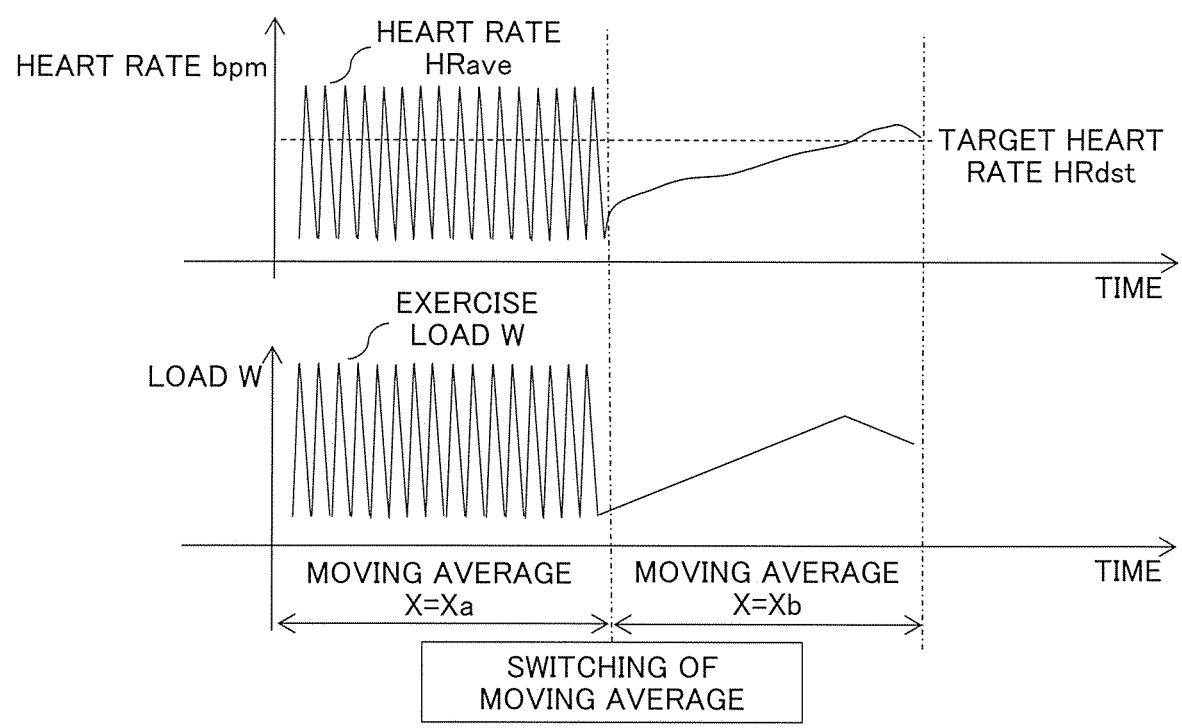
FIG. 9 is a schematic graph for showing an example of changes in contents of exercise load control in relation to a moving average.

A specific description is given with reference to FIG. 7 to FIG. 9 on why this embodiment is configured so that the moving average can be set for AF patients and for SR patients separately. FIG. 7 is a graph for showing an example of changes in standard deviation in relation to the moving average of the heart rate of an SR patient. FIG. 8 is a graph for showing an example of changes in standard deviation in relation to the moving average of the heart rate of an AF patient. FIG. 9 is a schematic graph for showing an example of changes in contents of exercise load control in relation to the moving average. In FIG. 7 and FIG. 8, the moving average is plotted along the axis of abscissa and the standard deviation is plotted along the axis of ordinate. In FIG. 9, an example of changes in heart rate with time is shown in an upper section and an example of changes in load intensity with time is shown in a lower section.

The standard deviation is a numerical value indicating the degree of data dispersion. As shown in FIG. 7 and FIG. 8, the AF patient does not exhibit a trend of convergence of the standard deviation value until the moving average exceeds 30, whereas the SR patient exhibits a trend of convergence of the standard deviation value when the moving average is from 5 to 10. The degree of fluctuations in heart rate, that is, the width and frequency of fluctuations in heart rate, greatly affect PI control. This is why this embodiment is configured so that the moving average can be set for AF patients and for SR patients separately. With the configuration that enables the setting of the moving average in this manner, more appropriate PI control can be performed for AF patients and for SR patients both. This means that an exercise load more appropriate for the exerciser can be set.

When the moving average set for SR patients is given as Xa and the moving average set for AF patients is given as Xb, Xa and Xb normally has a relationship "Xa<Xb". The moving average of a heart rate being measured cannot be calculated with the moving average Xb until the number of times of heart rate measurement reaches the moving average Xb. Accordingly, in this embodiment, as shown in FIG. 9, a moving average X which is actually set is set to the moving average Xa until the number of times of heart rate measurement reaches the moving average Xb. Fluctuations in the moving average of the heart rate can be further reduced by switching the moving average X from the moving average Xa to the moving average Xb. A heart rate acquired by measurement is hereinafter referred to as "instantaneous heart rate" and the moving average of the heart rate is referred to as "average heart rate" in order to avoid confusion.

The deviation HRd is calculated with the use of the moving average of the heart rate. When the target heart rate is given as HRdst and the moving average of the heart rate is given as HRave, the deviation HRd is calculated by, for example, "HRd=HRdst−HRave". The determination of the load intensity, that is, calculation of the load command value uses the deviation HRd. Fluctuations in load intensity can accordingly be reduced as well by reducing fluctuations in the moving average of the heart rate. This means that, for the exerciser, the ease of pedaling the pedals 1 is prevented from decreasing. The exerciser can consequently use the exercise therapy apparatus 10 more comfortably.

Figure 10:
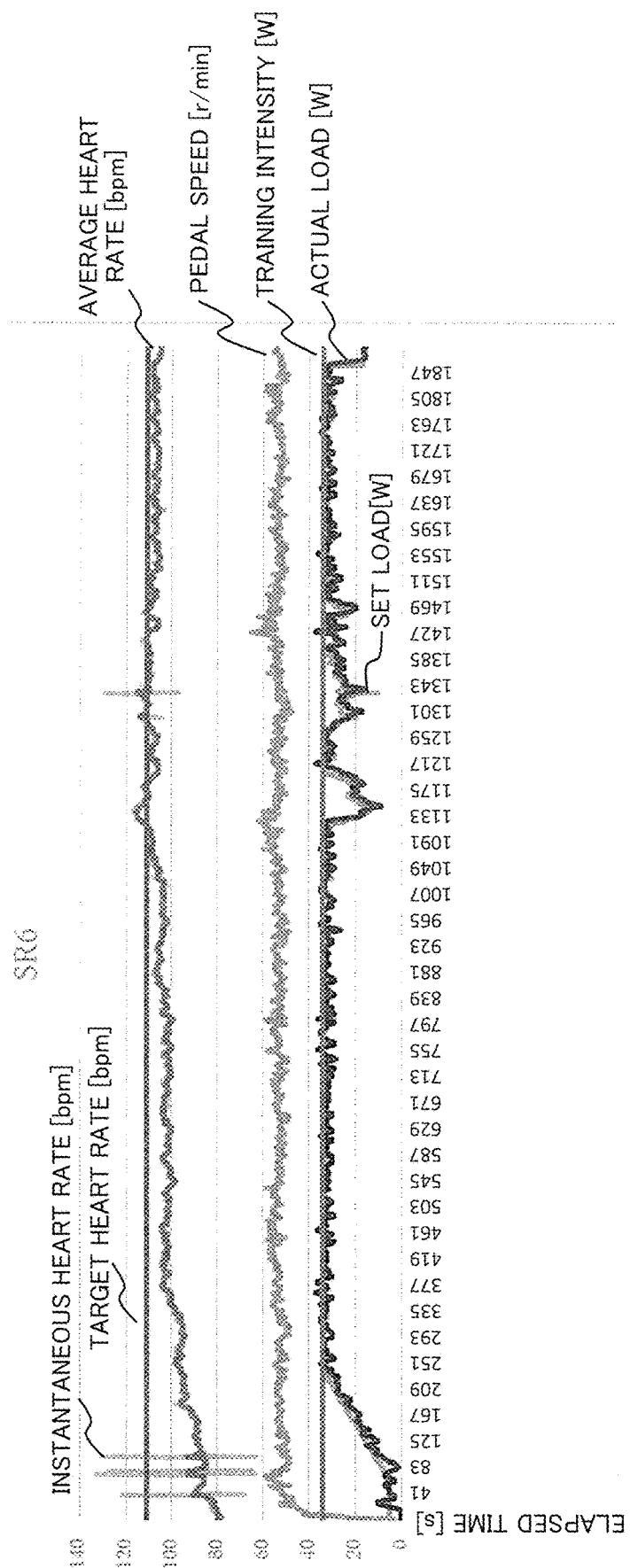
FIG. 10 is a graph for showing an example of contents of load control and an example of changes in heart rate that are observed when an SR patient exercises at parameter settings designed for SR patients.
Figure 11:
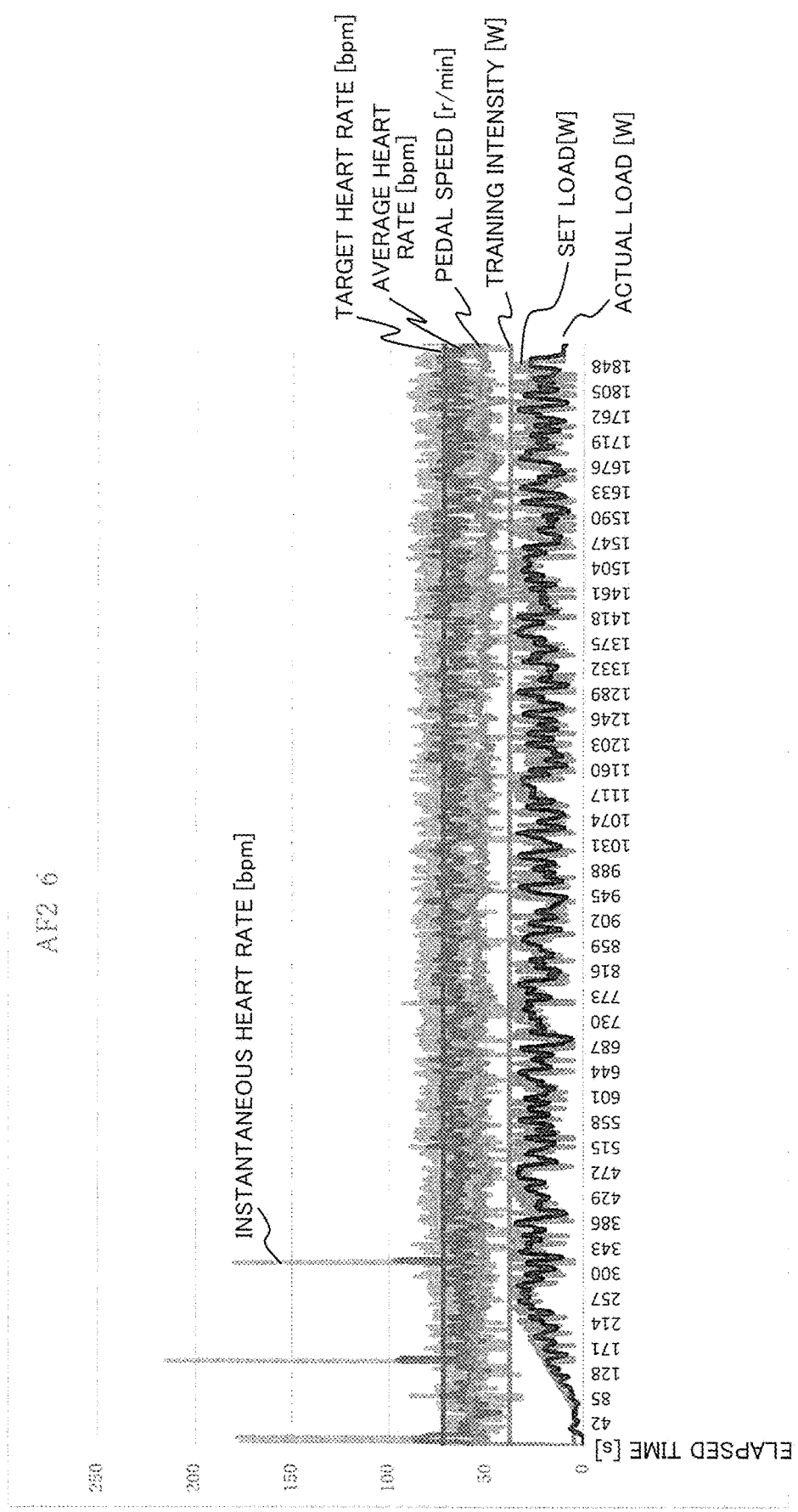
FIG. 11 is a graph for showing an example of contents of load control and an example of changes in heart rate that are observed when an AF patient exercises at parameter settings designed for SR patients.
Figure 12:
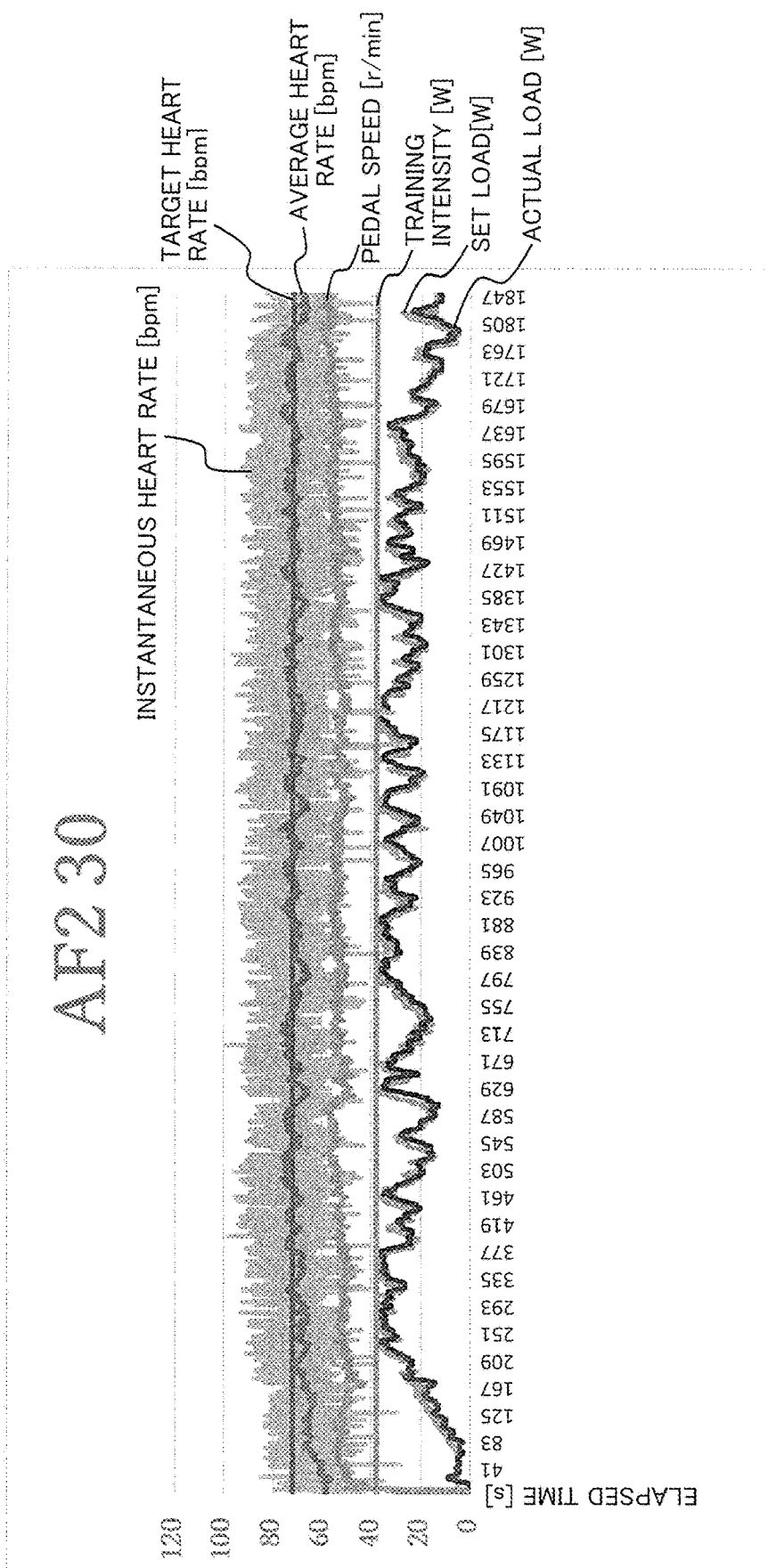
FIG. 12 is a graph for showing an example of contents of load control and an example of changes in heart rate that are observed when an AF patient exercises at parameter settings designed for AF patients.

A specific description is given next with reference to FIG. 10 to FIG. 12 about influences of the proportional constant and the integral constant which are parameters on heart disease patients. FIG. 10 is a graph for showing an example of contents of load control and an example of changes in heart rate that are observed when an SR patient exercises. FIG. 11 is a graph for showing an example of contents of load control and an example of changes in heart rate that are observed when an AF patient exercises at parameter settings designed for SR patients. FIG. 12 is a graph for showing an example of contents of load control and an example of changes in heart rate that are observed when an AF patient exercises at parameter settings designed for AF patients.

In FIG. 10 to FIG. 12, time is plotted along the axis of abscissa. In FIG. 10 to FIG. 12, the instantaneous heart rate and the average heart rate are both shown as a heart rate. A set load which is a load specified by the load command value is shown as the contents of load control in FIG. 10 to FIG. 12. In FIG. 10 and FIG. 11, an actual load which is an actually applied load is additionally shown as the contents of load control. The pedal speed is shown as well.

As shown in FIG. 10, when parameters designed for SR patients are set, heart rate fluctuations of the SR patient are confined to a narrow range for both of the instantaneous heart rate and the average heart rate. The SR patient can therefore appropriately exercise at a constant heart rate.

When parameters designed for SR patients are set, as shown in FIG. 11, the instantaneous heart rate of the AF patient fluctuates, resulting in large fluctuations in set load, and the changes in set load cause large fluctuations in average heart rate as well. When parameters designed for AF patients are set, on the other hand, as shown in FIG. 12, the fluctuations of the average heart rate stay within a very narrow range despite large fluctuations in the instantaneous heart rate of the AF patient. It is therefore important in exercise therapy of an AF patient to set parameters designed for AF patients. Setting of parameters more appropriate for AF patients enables an AF patient to experience exercise therapy of a higher quality. In order to accomplish exercise therapy of a higher quality, control that causes quicker arrival of the average heart rate at the target heart rate, prolonging of a period of time in which the average heart rate is within a close range from the target heart rate, and the like is required.

In this embodiment, settings of parameters, that is, the proportional constant and the integral constant, for AF patients and for SR patients can be switched by operating the AF patient button 41. This enables the exerciser to exercise at parameters suitable for the exerciser even when no supervisor is present. A high level of user friendliness is accordingly accomplished when the exercise therapy apparatus 10 is used. This enables the exerciser to use the exercise therapy apparatus 10 at appropriate settings more quickly, and lightens the burden of arranging such an exercise for the exerciser on the supervisor. As a result, both the exerciser and the supervisor can use time more effectively.

Figure 13:
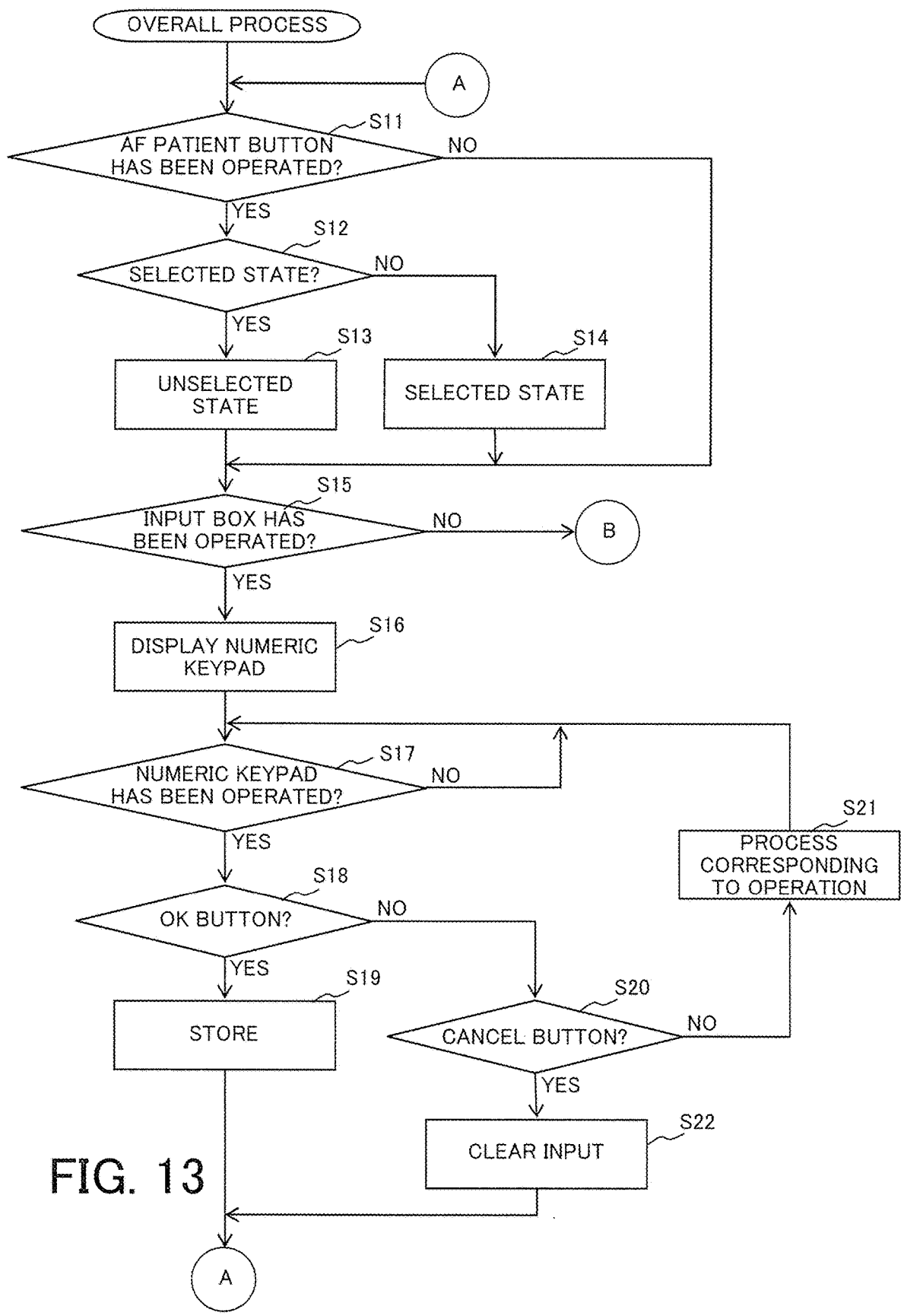
FIG. 13 is a flow chart for illustrating an example of overall process.
Figure 14:
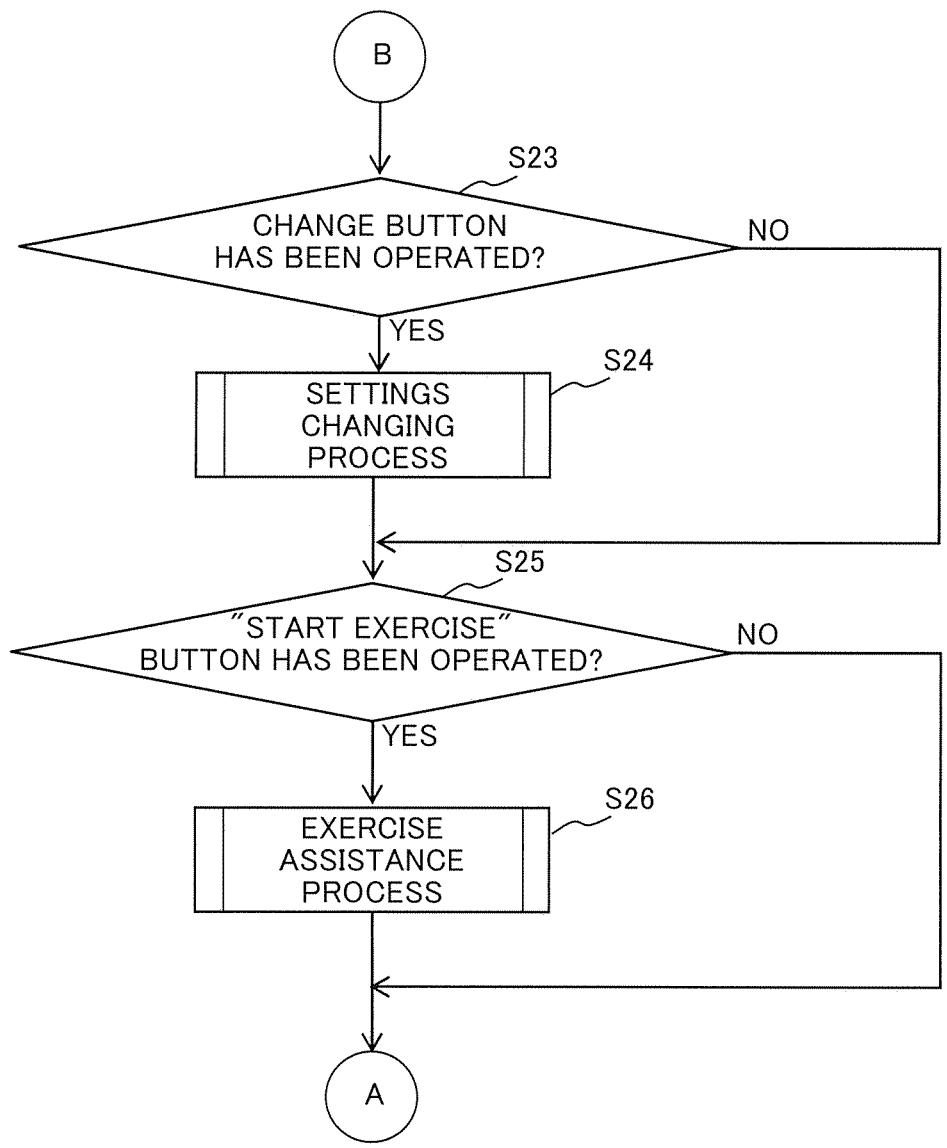
FIG. 14 is a flow chart for illustrating an example of the overall process.

FIG. 13 and FIG. 14 are flow charts for illustrating an example of overall process. This overall process is an overview of a flow of main process that is executed by the microcomputer 32 after the exercise therapy apparatus 10 is activated, that is, after the normal screen is displayed on the touch panel monitor 31. The overall process is implemented by the CPU 36, which is installed in the microcomputer 32, executing a program for control that is stored in the memory 35. A specific description on the overall process is given next with reference to FIG. 13 and FIG. 14. An actor of the process is the CPU 36.

First, in Step S11, whether the AF patient button 41 has been operated is determined. When the user, that is, the exerciser or the supervisor, operates the AF patient button 41, the operation is identified through analysis by the CPU 36. The result of the determination in Step S11 is accordingly "YES", and the process proceeds to Step S12. When the AF patient button 41 is not operated by the user, the result of the determination in Step S11 is "NO", and the process proceeds to Step S15.

In Step S12, the CPU 36 determines whether the AF patient button 41 is in a selected state at present. When the AF patient button 41 is displayed highlighted as illustrated in FIG. 5, the result of the determination in Step S12 is "YES" and the process proceeds to Step S13. When the AF patient button 41 is not displayed highlighted, the result of the determination in Step S12 is "NO" and the process proceeds to Step S14.

In Step S13, the CPU 36 switches the AF patient button 41 into an unselected state. That is, the AF patient button 41 is switched from highlighted display to normal display. The process then proceeds to Step S15. In Step S14, on the other hand, the CPU 36 switches the AF patient button 41 into a selected state by switching the AF patient button 41 from normal display to highlighted display. The process then proceeds to Step S15.

In Step S15, the CPU 36 determines whether operation, for example, tap operation, has been performed on one of the input boxes 42a or 42b. When the user performs the tap operation, the result of the determination in Step S15 is "YES" and the process proceeds to Step S16. When the user does not perform the tap operation, the result of the determination in Step S15 is "NO" and the process proceeds to Step S23 of FIG. 14.

In Step S16, the CPU 36 displays a numeric keypad for inputting data to the input boxes 42a and 42b on the touch panel monitor 31. The numeric keypad is a screen in which, for example, a delete key for deleting input data, an OK button, and a cancel button are arranged in addition to numeric keys of from 0 to 9. With that screen being displayed, data input is ended in this embodiment by operating the OK button or the cancel button. After the numeric keypad is displayed, the process proceeds to Step S17.

In Step S17, the CPU 36 determines whether the numeric keypad has been operated by the user in some manner When the user performs some operation on the numeric keypad, the result of the determination in Step S17 is "YES", and the process proceeds to Step S18. When the numeric keypad is not operated by the user, the result of the determination in Step S17 is "NO", and the determination process of Step S17 is executed again. In this manner, after the numeric keypad is displayed, only operation on the numeric keypad is processed.

In Step S18, the CPU 36 determines whether it is the OK button that has been operated. When the OK button has been operated by the user, the result of the determination in Step S18 is "YES", and the process proceeds to Step S19. When an operation object other than the OK button has been operated by the user, the result of the determination in Step S18 is "NO", and the process proceeds to Step S20.

In Step S19, the CPU 36 stores the input data. After the input data is stored, the process proceeds to Step S23 of FIG. 14. As a result, a target heart rate or an exercise time that is an arbitrary value input by the user is set.

In Step S20, the CPU 36 determines whether it is the cancel button that has been operated. When the cancel button has been operated by the user, the result of the determination in Step S20 is "YES", and the process proceeds to Step S22. When the cancel button has not been operated by the user, the result of the determination in Step S20 is "NO", and the process proceeds to Step S21.

In Step S21, the CPU 36 executes processing that corresponds to operation performed on an operation object other than the OK button and the cancel button. The execution of this processing enables the user to input any numerical value as data. After the processing is executed, the process returns to Step S17 described above.

In Step S22, the CPU 36 clears the input data without storing the input data. After the execution of the clearing, the process proceeds to Step S23 of FIG. 14.

In Step S23 of FIG. 14, the CPU 36 determines whether the change button 43 has been operated. When the user operates the change button, the result of the determination in Step S23 is "YES", and the process proceeds to Step S24. Then, the CPU 36 executes settings changing processing which enables the user to change parameter settings. After the execution of the settings changing processing, the process proceeds to Step S25. The user here is mainly the supervisor.

In Step S25, the CPU 36 determines whether the "start exercise" button 44 has been operated. When the user operates the "start exercise" button 44, the result of the determination in Step S25 is "YES", and the process proceeds to Step S26. When the user does not operate the "start exercise" button 44, the result of the determination in Step S25 is "NO", and the process returns to Step S11 of FIG. 13.

In Step S26, the CPU 36 executes exercise assistance process for assisting the exerciser in a constant heart rate exercise so that the average heart rate is kept at the set target heart rate for a period of time set as the exercise time. After the execution of the exercise assistance process, the process returns to Step S11 of FIG. 13.

Figure 15:
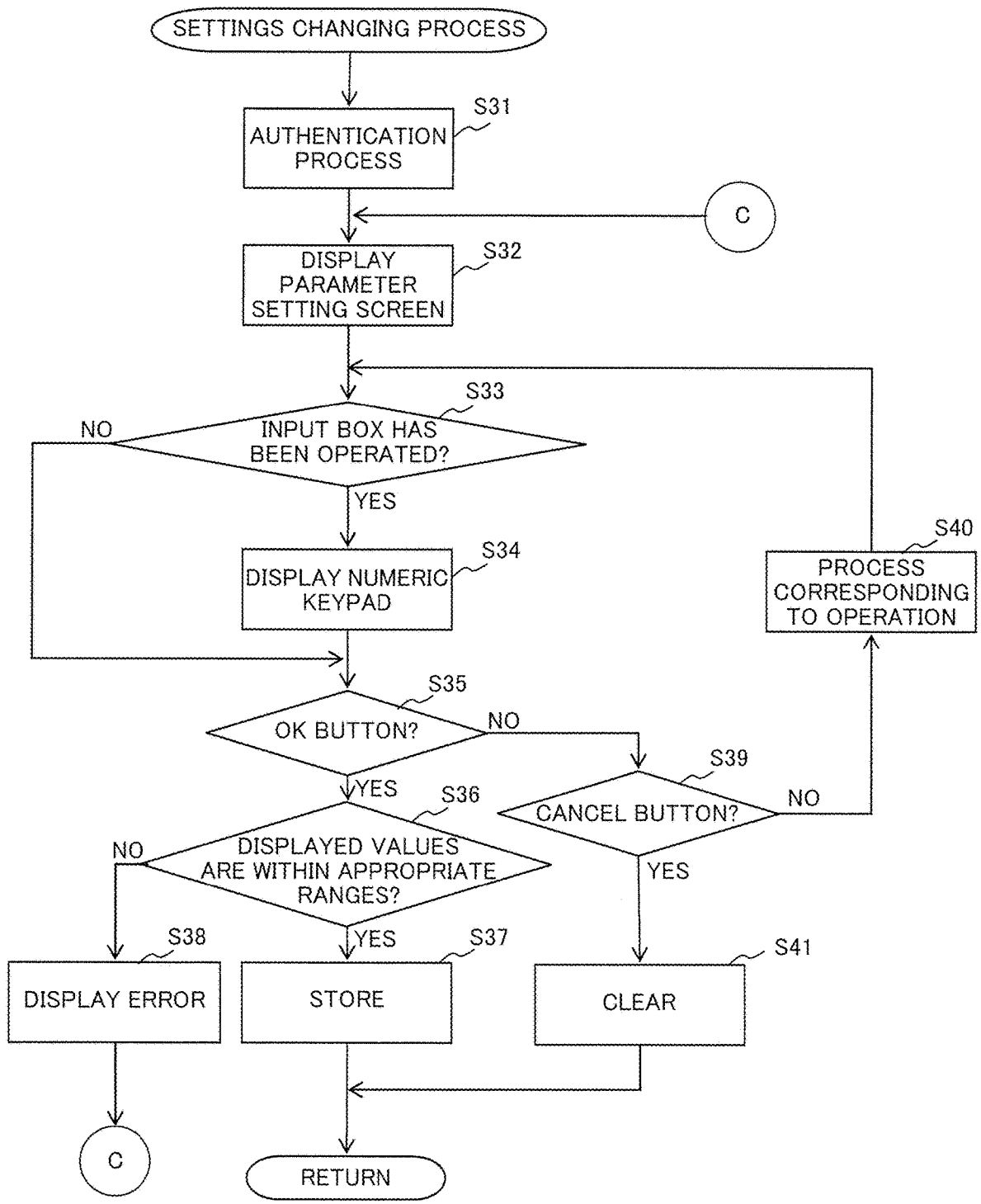
FIG. 15 is a flow chart for illustrating an example of settings changing process.

FIG. 15 is a flow chart for illustrating an example of the settings changing process to be executed as Step S24 described above. The settings changing process is described next in detail with reference to FIG. 15.

As shown in FIG. 10 to FIG. 12, a change of parameter settings has a great influence. For that reason, only limited persons are allowed to change parameter settings in this embodiment. To that end, in Step S31, the CPU 36 first executes authentication process for checking whether the user who has operated the change button 43 is an entitled person entitled to change parameter settings.

The authentication processing is a process of checking whether the user is an entitled person with the use of, for example, a password. When the user is not successfully confirmed as an entitled person, or when the user cancels the authentication, the settings changing process is ended by the execution of the authentication process. When the user is successfully confirmed as a supervisor, the process proceeds to Step S32 after the execution of the authentication process.

In Step S32, the CPU 36 displays the parameter setting screen illustrated in FIG. 6 on the touch panel monitor 31. Currently set numerical values are displayed in the input boxes 61a to 61f. The process next proceeds to Step S33, and the CPU 36 determines whether one of the input boxes 61a to 61f has been operated. When the user operates one of the input boxes 61a to 61f, the result of the determination in Step S33 is "YES", and the process proceeds to Step S34. When the user operates none of the input boxes 61a to 61f, the result of the determination in Step S33 is "NO", and the process proceeds to Step S35.

In Step S34, the CPU 36 displays a numeric keypad on the touch panel monitor 31. The numeric keypad displayed here differs from the numeric keypad described above, and is a screen in which, for example, only a delete key for deleting input data is arranged aside from numeric keys of from 0 to 9. The OK button 62 and the cancel button 63 remain operable after the numeric keypad is displayed. After the numeric keypad is displayed, the process proceeds to Step S35.

In Step S35, the CPU 36 determines whether the OK button has been operated. When the user operates the OK button, the result of the determination in Step S35 is "YES", and the process proceeds to Step S36. When the user operates an operation object other than the OK button, the result of the determination in Step S35 is "NO", and the process proceeds to Step S39.

In Step S36, the CPU 36 determines whether every one of the numerical values displayed in the input boxes 61a to 61f is within an appropriate range. When at least one of the numerical values input in the input boxes 61a to 61f by the user is a clearly inappropriate value, the result of the determination in Step S36 is "NO", and the process proceeds to Step S38. When every one of the numerical values displayed in the input boxes 61a to 61f is appropriate, the result of the determination in Step S36 is "YES", and the process proceeds to Step S37.

In Step S37, the CPU 36 stores, in the memory 35, the numerical values displayed in the input boxes 61a to 61f. The parameter groups 324a and 324b stored in the storage unit 324 are both updated by the storing of the displayed numerical values. After the storing is executed, the settings changing process is ended.

In Step S38, the CPU 36 displays, on the touch panel monitor 31, an error message for prompting the user to input a new value that is a replacement of the inappropriate numerical value. The process then returns to Step S32 described above. As a result, the parameter setting screen is displayed on the touch panel monitor 31 again.

In Step S39 to which the process proceeds from Step S35 due to the determination result being "NO", whether the cancel button 63 has been operated is determined. When the user operates the cancel button 63, the result of the determination in Step S39 is "YES", and the process proceeds to Step S41. When the user does not operate the cancel button 63, the result of the determination in Step S39 is "NO", and the process proceeds to Step S40.

In Step S40, the CPU 36 executes a process for dealing with the user's operation of an operation object other than the OK button 62 and the cancel button 63. The user's operation of the numeric keypad can be dealt with by executing this process. That is, this enables the user to update, at his or her discretion, the numerical values displayed in the input boxes 61a to 61f. When there is no object operated by the user, the process is not executed in Step S40. After the process of Step S40 is executed, the process returns to Step S33 described above.

In Step S41, the CPU 36 clears the numerical values displayed as data in the input boxes 61a to 61f without storing the displayed numerical values. Accordingly, none of the parameter groups 324a and 324b stored in the storage unit 324 is updated. After the clearing is executed, the settings changing process is ended.

In the overall process, the process proceeds to Step S25 after the execution of the settings changing process. Before proceeding to Step S25, or in proceeding to Step S25, the CPU 36 displays the normal screen on the touch panel monitor 31.

Figure 16:
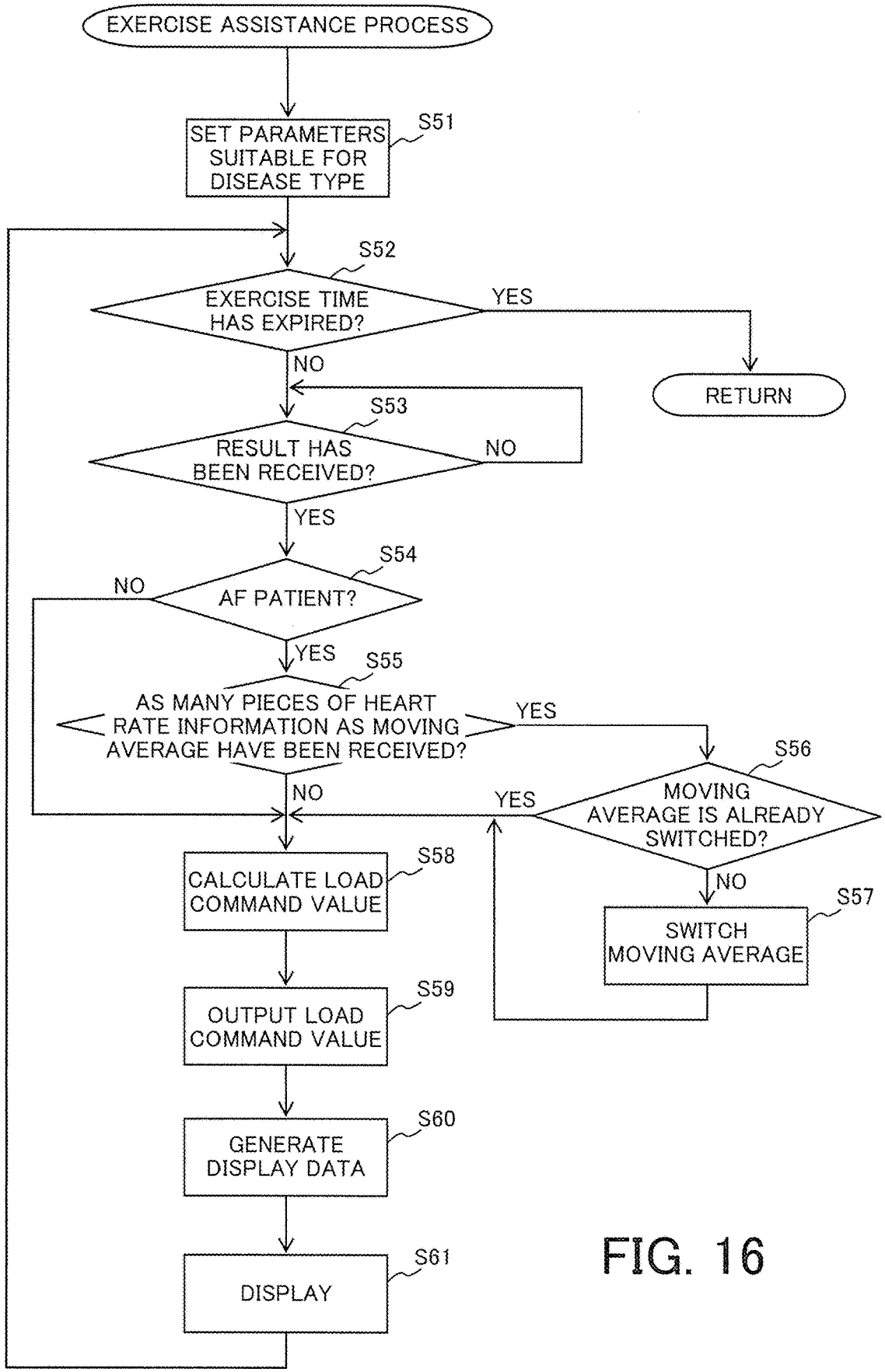
FIG. 16 is a flow chart for illustrating an example of exercise assistance process.

FIG. 16 is a flow chart for illustrating an example of the exercise assistance process to be executed as Step S26 described above. The exercise assistance process is described last in detail with reference to FIG. 16. The exercise assistance process is, as described above, the process for assisting the exerciser in an exercise so that the average heart rate of the exerciser remains the target heart rate for the set exercise time.

First, in Step S51, the CPU 36 sets parameters based on a disease type input by the user, that is, whether the exerciser is an AF patient. The CPU 36 also sets an exercise time, a target heart rate, and various initial values. The process then proceeds to Step S52.

The parameters to be set include, as described above, the moving average, the proportional constant, and the integral constant. Whether the exerciser is an AF patient is identifiable from the preceding selected/unselected state of the AF patient button 41. When the exerciser is identified as an AF patient, a moving average designed for AF patients is set as the moving average as described above. A value corresponding to a numerical value that is displayed in the input box 42a is set as the target heart rate. A value corresponding to a numerical value that is displayed in the input box 42b is set as the exercise time. The various initial values include the load command value and the current time. The current time is referred to in order to assist the exerciser in an exercise for the set exercise time.

In Step S52, the CPU 36 determines whether the exercise time has elapsed. When the length of time elapsed since the current time set as one of the initial values is equal to or longer than the exercise time, the result of the determination in Step S52 is "YES", and the exercise assistance process ends at this point. Otherwise, the result of the determination in Step S52 is "NO", and the process proceeds to Step S53.

In Step S53, the CPU 36 determines whether the heart rate information indicating a result of measuring the instantaneous heart rate of the exerciser has been received from the heart rate detection sensor 2. When the heart rate information is received by the interface controller 37, the result of the determination in Step S53 is "YES", and the process proceeds to Step S54. When the heart rate information is not received by the interface controller 37, the result of the determination in Step S53 is "NO", and the CPU 36 executes the determination processing of Step S53 again. The CPU 36 waits for the reception of the heart rate information from the heart rate detection sensor 2 in this manner In Step S54, the CPU 36 determines whether the exerciser is an AF patient. When the "start exercise" button 44 is operated with the AF patient button 41 being highlighted, the exerciser is identified as an AF patient. In that case, the result of the determination in Step S54 is accordingly "YES", and the process proceeds to Step S55. Otherwise, the result of the determination in Step S54 is "NO", and the process proceeds to Step S58.

In Step S55, the CPU 36 determines whether as many pieces of heart rate information as the moving average set for AF patients have been received. When the number of pieces of heart rate information received after the execution of the exercise assistance process is started reaches the moving average, the result of the determination in Step S55 is "YES", and the process proceeds to Step S56. When the number of received pieces of heart rate information falls short of the moving average, the result of the determination in Step S55 is "NO", and the process proceeds to Step S58.

In this embodiment, as shown in FIG. 9, when the exerciser is an AF patient, the moving average settings are switched from the moving average for SR patients to the moving average for AF patients upon reception of as many pieces of heart rate information as the moving average set for AF patients. The CPU 36 therefore determines in Step S56 whether the moving average settings are already switched. When the switching of the moving average settings to the moving average for AF patients is finished, the result of the determination in Step S56 is "YES", and the process proceeds to Step S58. When the switching of the settings is not finished, the result of the determination in Step S56 is "NO", and the process proceeds to Step S57.

In Step S57, the CPU 36 switches the moving average settings to the moving average for AF patients. The process then proceeds to Step S58.

In Step S58, the CPU 36 uses the number of pieces of heart rate information including newly received heart rate information that is equal to the moving average to calculate the load command value. The load command value is calculated by, as described above, calculating the average heart rate, calculating the deviation with the use of the calculated average heart rate and the target heart rate, using the deviation to calculate the increment/decrement $\Delta W$ by Expression (1), and using the increment/decrement $\Delta W$ to obtain the load command value by Expression (2). The process then proceeds to Step S59.

In Step S59, the CPU 36 outputs the calculated load command value to the load driving device 7 via the interface controller 37 and the communication interface 34. Next, in Step S60, the CPU 36 generates display data for updating contents displayed on the touch panel monitor 31. In Step S61 to which the process proceeds from Step S60, the CPU 36 updates the contents displayed on the touch panel monitor 31 by outputting, for example, image data of the generated display data to the touch panel monitor 31. The process then returns to Step S52.

During the exercise of the exerciser, the heart rate, the pedal speed, the target load, and burned calories are updated as required as illustrated in FIG. 4 and FIG. 5. The display data generated in Step S56 is, for example, pieces of data that are the pedal speed, the target load, and burned calories. Here, the heart rate is the average heart rate, and the target load is a value corresponding to the load command value.

In this embodiment, the exerciser inputs data on whether the exerciser is an AF patient by operating the AF patient button 41. AF patients may further be classified into a plurality of categories. That is, this embodiment may be configured so that the exerciser inputs, in addition to the data on whether the exerciser is an AF patient, data indicating an AF patient category. For example, New York Heart Association (NYHA) functional classifications of heart failure may be employed for the plurality of AF patient categories.

In this embodiment, PI control is used to calculate the load command value. The calculation of the load command value is not limited to the use of PI control. The calculation of the load command value may use proportional-integral-differential (PID) control or P control. How a fixed constant and the integral constant that are parameters are to be used is not particularly limited as well.

In this embodiment, data acquired during the exercise of the exerciser is cleared when the exercise is ended. However, this embodiment may be configured so that the data is stored or transmitted to an external device. When information with which an individual is identifiable is to be additionally input, for example, when the personal information can be input via a card or the like, the data may be stored or transmitted in association with the personal information. When this embodiment is configured so that the data can be checked later, assistance can be provided in setting parameters that are optimum for a heart disease patient. When information with which an individual is identifiable is to be input, parameters may be stored for each individual separately so that parameters associated with input information are automatically set. With the parameters being set in this manner, the exerciser can experience an exercise of a higher quality that is more solidly executed.

REFERENCE SIGNS LIST

1 pedal, 2 heart rate detection sensor, 3 operating unit, 4 decelerator, 5 transmission mechanism, 6 motor, 7 load driving device, 10 exercise therapy apparatus, 11 main body, 31 touch panel monitor, 32 microcomputer (exercise load control device), 35 memory, 36 CPU, 37 interface controller, 321 measurement result acquisition unit, 322 measurement result processing unit, 323 main control unit, 324 storage unit, 324a, 324b parameter group, 325 display control unit, 326 operation contents analysis unit

The invention claimed is:

1. An exercise load control device, comprising:
patient information input circuitry configured to input patient information which indicates whether a patient using an exercise therapy apparatus is an atrial fibrillation patient;
heart rate information acquisition circuitry configured to acquire heart rate information which indicates a heart rate of the patient using the exercise therapy apparatus; and
load control circuitry configured to control a magnitude of a load to be applied by the exercise therapy apparatus to the patient, based on the patient information input by the patient information input circuitry and the heart rate information acquired by the heart rate information acquisition circuitry,
wherein the load control circuitry is configured to control the magnitude of the load so that the heart rate indicated by the heart rate information matches a set target value by changing, based on the patient information, at least one coefficient out of a first coefficient by which a difference between the heart rate and the set target value is to be multiplied and a second coefficient by which the difference, or an integral value using the difference, is to be multiplied.

2. The exercise load control device according to claim 1, wherein the load control circuitry is configured to control the magnitude of the load so that an average heart rate that is a heart rate calculated with use of as many heart rates indicated by the heart rate information as a moving average of the indicated heart rate matches the set target value by changing, based on the patient information, a moving average for calculating the moving average of the indicated heart rate.

3. A method, comprising:
inputting patient information by patient information input circuitry, which indicates whether a patient using an exercise therapy apparatus is an atrial fibrillation patient;
acquiring heart rate information by a heart rate information acquisition circuitry, which indicates a heart rate of the patient using the exercise therapy apparatus; and
controlling by a load control circuitry, a magnitude of a load to be applied by the exercise therapy apparatus to the patient, based on the patient information which has been input and the heart rate information,
wherein the controlling controls the magnitude of the load so that the heart rate indicated by the heart rate information matches a set target value by changing, based on the patient information, at least one coefficient out of a first coefficient by which a difference between the heart rate and the set target value is to be multiplied and a second coefficient by which the difference, or an integral value using the difference, is to be multiplied.

4. The method according claim 3, wherein:
the controlling controls the magnitude of the load so that an average heart rate that is a heart rate calculated with use of as many heart rates indicated by the heart rate information as a moving average of the indicated heart rate matches the set target value by changing, based on the patient information, a moving average for calculating the moving average of the indicated heart rate.

* * * * *